US006580081B1

(12) United States Patent
Thorwirth (10) Patent No.: US 6,580,081 B1
(45) Date of Patent: Jun. 17, 2003

(54) ARRANGEMENT FOR THE DETECTION OF FLUORESCENE RADIATION OF MATRIX-SHAPED SPECIMAN CARRIERS

(75) Inventor: Guenter Thorwirth, Laasdorf (DE)

(73) Assignee: Jena-Optronik GmbH, Jena (DE)

( * ) Notice: Subject to any disclaimer, the term of this patent is extended or adjusted under 35 U.S.C. 154(b) by 208 days.

(21) Appl. No.: 09/630,043

(22) Filed: Aug. 1, 2000

(30) Foreign Application Priority Data

Aug. 2, 1999 (DE) .......................................... 199 36 999

(51) Int. Cl.⁷ .............................................. G01N 21/64
(52) U.S. Cl. ................................................... 250/458.1
(58) Field of Search ........................... 250/458.1, 459.1, 250/461.1, 461.2

(56) References Cited

U.S. PATENT DOCUMENTS

| 4,087,685 A | * | 5/1978 | Froot | 250/302 |
| 4,426,154 A | * | 1/1984 | Steen | 250/461.1 |
| 5,672,880 A | * | 9/1997 | Kain | 250/458.1 |
| 5,917,605 A | * | 6/1999 | Colvin, Jr. | 250/458.1 |

FOREIGN PATENT DOCUMENTS

| DE | 26 42 170 | 4/1977 |
| DE | 35 23 243 | 1/1987 |
| DE | 41 15 401 | 11/1992 |
| DE | 197 45 373 | 4/1999 |
| DE | 197 48 211 | 5/1999 |

OTHER PUBLICATIONS

Abstracts of "Handbuch der Mikroskopie" Editors: H. Beyer, H. Riesenberg (pp. 41–16; 144–160; and 221–234).

Abstract of article "Mikroskopie" (Nachr. Chem. Tech. Lab. 38 (1990) 10, pp M2–M14).

* cited by examiner

*Primary Examiner*—Constantine Hannaher
(74) *Attorney, Agent, or Firm*—Reed Smith LLP (57) ABSTRACT

An arrangement for the detection of the fluorescence radiation of matrix-shaped specimen carriers with a large number of individual specimens, in particular, for the analysis of chemical and biological specimen carriers is disclosed. The object of the invention, to find a new possibility for detection of fluorescence radiation of matrix-shaped specimen carriers with a large number of individual specimens which permits a highly sensitive quantitative readout of the fluorescence radiation which is characteristically influenced by the individual specimen substances, is met in that, while simultaneously exciting the fluorescence radiation of a large number of substrate pixels, the transmitting optics for transmitting the fluorescence radiation emitted by individual substrate pixels to a multi-element receiver contain an imaging objective by which every substrate pixel is correlated with a determined group of receiver elements of the multi-element receiver and which is outfitted with an additional aperture stop for limiting the angular area of the recorded fluorescence radiation, so that the receiver elements which are correlated respectively with a determined substrate pixel receive substantially no fluorescent light of neighboring substrate pixels, and a darkfield illumination is provided for exciting a large number of substrate pixels with an excitation beam bundle which cuts out the aperture of the objective as well as a substantial angular area surrounding the objective aperture.

18 Claims, 4 Drawing Sheets

ARRANGEMENT FOR THE DETECTION OF FLUORESCENE RADIATION OF MATRIX-SHAPED SPECIMAN CARRIERS

BACKGROUND OF THE INVENTION a) Field of the Invention

The invention is directed to an arrangement for the detection of fluorescence radiation of matrix-shaped specimen carriers, in particular for the analysis of chemical and biological specimen carriers such as nanotiter plates or biochips.

b) Description of the Related Art

The use of microtiter plates, as they are called, and associated handling technology is an established technique (pharmacological research, clinical practice, etc.) for tasks relating to biotechnical analysis (screening) of large quantities of specimens, preferably for gene analysis (e.g., for diagnosing viruses). This technique is distinguished by the feature that, depending on the embodiment form, 96 (commonest type), 384 or 1536 different specimen substances can be accommodated in a microtiter plate having dimensions of 8 cm×12 cm. Depending on the type of microtiter plate, specimen quantities in the order of magnitude of 100 $\mu$l are required to fill the individual cavities or wells.

By way of increasing effectiveness, research and development work is in progress internationally for the purpose of substantially increasing the quantity of (simultaneously usable) wells while at the same time substantially reducing the required specimen quantities and substantially increasing the specimen throughput. These aims are to be achieved by a transition from microtiter plates to biochips (produced, e.g., with microphotolithography techniques) and fast readout and processing (high throughput screen, HTS) of the biochips.

In order to read out biochips (as well as microtiter plates or any other chemical specimen carriers), the specimen material is irradiated with light in the UV to NIR range, depending on the type of specimen, to cause stimulated radiation in determined substances in the specimens (fluorescent markers are preferably added to the specimen material) due to the effect of the illumination radiation and thereby to detect the presence of determined substances (or components with which a marker substance has coupled) and to determine the proportion thereof in the specimen material.

An individual biochip can contain several tens of thousands of spots (comparable to the wells of the microtiter plate) on a surface of several mm$^2$ to cm$^2$, wherein only specimen quantities on the order of several nanoliters (nl) are required over the sum of all spots. Due to the number of specimens to be evaluated which has accordingly increased enormously, the camera principle, as it is called, has gained increasing popularity for fast readout of the matrix-shaped arrangement of the pixels, aside from the equally well-established scanner principle (with serial laser illumination of the spots and detection of the excited radiation by means of an individual receiver, e.g., a photon counter [SEV or PMT]). In the camera principle, the pixels of the biochip are illuminated in parallel and many or all pixels of the specimen carrier are read out simultaneously using an optoelectronic receiver matrix (e.g., CCD). The following devices make use of the camera principle, for example:

DIANA (Raytest, USA)

ARTHUR fluoroimager (EG&G Wallac, FI)

ArrayWoRx (Applied Precision, USA).

An example for the application of the camera principle is a nanotiter plate readout system from a BMBF joint project, LINDAU (laser-induced fluorescence detection on microstructured specimen carriers for analysis in environmental metrology), which is described in the technical article "Optical Microsystems for Environmental Metrology" (Laser und Optoelektronik, 30 (1), 1998, pages 33–35). According to this publication, direct incident illumination is used via a dichroic mirror for extensive separation of the radiation wavelengths of illumination and fluorescence radiation. Although the type of illumination used here (which is also generally recommended) in the analysis of fluorescence radiation of an object is incident illumination, since it causes the fewest problems with differing transmission of the examined specimens, reflected or scattered components of the illumination light have a noticeable influence on the measurement results—due to the specific surface of the biochip pixels as will be described more exactly in the following, even when using good blocking filters for the wavelengths of the illumination radiation—because the receiver must have a very high sensitivity in view of the much weaker fluorescence radiation.

Another common step in the prior art for increasing sensitivity of detection of fluorescence radiation is the optical imaging of specimen pixels on the receiver by means of high-aperture objectives in order to concentrate as much of the fluorescent light as possible on the receiver, this fluorescent light being weak in itself. For example, suppliers of biochip analysis instruments, e.g., the suppliers of laser scanning systems, General Scanning, Inc. (USA), point to the high aperture of the utilized objective as a selling point. Also, according to general expert opinion, as shown in O. Beyer, "Handbuch der Mikroskopie [Handbook of Microscopy]", (Verlag Technik Berlin, third printing, 1988, pages 221 ff.) for fluorescence microscopy, with objectives of like magnification those having the higher aperture are preferred, wherein objective immersion is suggested for a further aperture increase.

The surface of every individual spot of a biochip (after a large number of technical steps for preparing the biochip) is generally not flat in an optical sense because it initially has a curved teardrop shape which gradually dries up over the course of processing steps and accordingly takes on an uneven (wrinkled) surface. Accordingly, with the usual incident illumination, problems result in the evaluation channel in that unwanted components of the illumination radiation reach the receiver because of reflections and scattering at the mostly uneven, rough surface. This fact is taken into account in the above-mentioned fluoroimager by EG&G Wallac (see, e.g., company brochure 1442-960-01 (April 1998) for ARTHUR multi-wavelength fluoroimager) to the extent that transmitted light illumination, indirect and lateral incident illumination are offered. A xenon radiator emitting a continuous spectrum with relatively uniform intensity and a UV radiator which is distinguished by intensive discrete spectral lines in the near UV and visible spectrum are used as radiation sources for lateral excitation of fluorescence, wherein the desired illumination wavelength can be selected by choosing an appropriate excitation filter. However, it can not be gathered from the publication whether or not, or to what extent, the quantity of generated fluorescence radiation of different specimens can be compared by means of these types of illumination.

OBJECT AND SUMMARY OF THE INVENTION

It is the primary object of the invention to find a new possibility for detection of fluorescence radiation of matrix-shaped specimen carriers with a large number of individual specimens which permits a highly sensitive quantitative readout of the fluorescence radiation which is characteristically influenced by the individual specimen substances. Another object of the invention consists in making the excitation intensity comparable when using different fluorescing substances.

In an arrangement for the detection of fluorescence radiation of matrix-shaped specimen carriers with a large number of individual specimens presenting metrically ordered pixels on a substance and emitting a fluorescence radiation that is characteristically influenced by the respective specimen substance, with an illumination device for simultaneous excitation of the fluorescence radiation of a large number of substrate pixels, containing a light source and a spectrally narrow-band excitation filter which can be exchanged depending on the fluorescing substance, with transmitting optics for transmitting the fluorescence radiation emitted by individual substrate pixels to a receiver with a large number of receiver elements and an exchangeable filter in front of the receiver for passing wavelengths of the fluorescing substance and blocking excitation wavelengths, the object stated above is met according to the invention in that the transmitting optics contain an imaging objective by which every substrate pixel is correlated to a determined group of receiver elements of the receiver and which is outfitted with an additional aperture stop for limiting the angular area of the fluorescence radiation detected by the objective, so that the receiver elements which are correlated respectively with a determined substrate pixel receive substantially no fluorescent light of neighboring substrate pixels, and in that the illumination device has a darkfield illumination unit for large-area illumination of a large number of substrate pixels by formation of an excitation beam bundle which is symmetric with respect to the axis of the objective and which cuts out the aperture of the objective as well as a substantial angular area surrounding the objective aperture.

A micro-objective is advantageously used as the objective in order to obtain a sufficiently magnified imaging with few imaging errors of the substrate pixels on the receiver. To prevent detectable crosstalk of the fluorescence radiation of neighboring substrate pixels on receiver elements not assigned to them, the additional aperture stop is preferably dimensioned in such a way that the effective numerical aperture of the micro-objective is reduced by 10 to 30%.

A micro-objective with an aperture stop plane located outside of the objective is advisably provided as objective, wherein the additional aperture stop can be arranged in this aperture stop plane in a simple manner.

A micro-objective with ten-times magnification and an aperture of 0.2 to 0.25 can advantageously be used. In this case, the effective aperture of the micro-objective is reduced by 15 to 30% by the additional aperture stop.

In a micro-objective which images to infinity, the transmitting optics are advisably supplemented by a tube lens arranged in a tube which is adjustable in length for generating a sharp optical imaging of the substrate pixels emitting the fluorescence radiation on the associated groups of receiver elements.

The darkfield illumination unit is advisably constructed symmetrically for reasons of homogeneity of the excitation radiation in the substrate plane. This can be carried out advantageously by means of light guides whose light outlet windows, which are distributed about the optical axis of the objective, are focused on a spot of the substrate. Also, a rotationally symmetric darkfield condenser for generating a ring-shaped excitation beam bundle is preferably used as darkfield illumination unit for transmitted light illumination of the substrate. A dry darkfield condenser is particularly suitable for this purpose. When a darkfield condenser is used it is advantageous to arrange additional optics in front of it as a collector.

In order to make fluorescence radiation measurements comparable when exciting with different excitation wavelengths, the spectral emission of the illumination device and the spectral sensitivity of the receiver are to be adapted to one another in such a way that their product gives approximately a constant over a wavelength range required for the fluorescence substances to be detected. For optimum excitation of fluorescence radiation of different fluorescing substances, an intensive continuous light source with an exchangeable bandpass filter adapted to the excitation wavelength of the fluorescing substance is advantageously used.

A halogen lamp or xenon lamp is advisably used as a broad-band light source. The light source is advantageously coupled with the darkfield illumination unit via a light guide so that the light source is separated spatially, and therefore preferably thermally, from the rest of the components. This coupling is preferably carried out by means of a liquid light-conducting cable in order to minimize transmission loss in the intensity of the excitation radiation in the desired wavelength range.

When using a light source coupling via light-conducting cable, the spectral emission of the light source, the spectral transmission of the light guide and the spectral sensitivity of the receiver are adapted to one another in such a way that the product of these three spectral quantities gives approximately a constant.

The optical subassemblies mentioned above are advantageously comprised in exchangeable modules for adapting to specific cases of application. The arrangement according to the invention is advisably divided into, successively, a light source module, preferably with connected light guides for transmitting the excitation light, a module for coupling in light and beam expansion, a substrate carrier module, an imaging module for the fluorescence radiation and a camera module, wherein the substrate carrier module in particular contains a substrate displacement unit for recording large-area substrates and for continuously successive processing of a plurality of substrates.

The basic idea of the invention is based on the insight that the recommendation applied for fluorescence analysis in the prior art, to realize the transmission of the very weak fluorescent light onto the receiver with objectives having the highest possible aperture, is not favorable in every case. As has been shown by theoretical and empirical results in trials with the camera principle, large aperture values of real imaging optics in a quantitative detection of fluorescence intensities of small and closely adjacent matrix elements lead to noticeable crosstalk (when imaging on a CCD matrix, components of the fluorescence radiation of a determined substrate pixel also reach neighboring receiver elements which should actually detect exclusively the fluorescence intensity of a neighboring substrate pixel).

In particular with a high objective aperture, the crosstalk causes the fluorescence measurements to be influenced in such a way that this falsifying of the individual specimen measurement values cannot be tolerated for quantitative fluorescence analysis. This problem is solved according to the invention in that the given aperture of a magnifying imaging objective is limited to such an extent that the crosstalk of the fluorescence radiation is sufficiently suppressed. In this respect, the extent to which the aperture is reduced depends essentially on the correction factor of the objective relative to imaging errors (aberrations). Accordingly, with the use of micro-objectives (which are generally easily corrected) reductions of less than 30% are entirely adequate, whereas in the case of photographic objectives aperture reductions of up to 50%, sometimes even up to 65%, are necessary for sufficient prevention of crosstalk.

It is not only in the latter case that a reduction in the aperture also entails a considerable light attenuation of the fluorescence radiation that must be compensated by suitable steps in the illumination of the substrates. In addition, the various fluorescing substances that are used are taken into account with respect to their specific optimum excitation wavelength and a uniformly intensive excitation with the different excitation wavelengths through the use of a suitable continuously intensive light source, transmitting media with correspondingly high transmission and matched spectral characteristics of the illumination and the receiver. For the last step, the spectral emission of the illumination device and the spectral sensitivity of the receiver are adapted to one another in such a way that their product gives approximately a constant over a wavelength range required for the fluorescing substances that are to be detected. It must be mentioned in this connection that—strictly speaking—the product of the spectral emission of the illumination on the excitation wavelength and the spectral sensitivity of the receiver on the emission wavelength of the fluorescence would have to give a constant. However, since the excitation wavelength and the fluorescence wavelengths of the usual fluorescent dyes are only separated by several tens of nm, this slight imprecision can be disregarded when the product of the spectral characteristics is sufficiently constant over the entire necessary wavelength range.

Accordingly, it is possible with the arrangement according to the invention to minimize the crosstalk of the fluorescence radiation of neighboring substrate pixels on the receiver and to compensate for the consequent inevitable deficit in the detected fluorescence intensity by more efficient illumination of the examined substrate pixels. Accordingly, a quantitative readout of the fluorescence radiation is realized in which every individual specimen substance on a specimen carrier with a large number of individual specimens can be analyzed in a highly sensitive manner with respect to the quantity of contained fluorescing substance and the results are comparable even when using different fluorescing substances.

The invention will be explained more fully in the following with reference to an embodiment example.

DESCRIPTION OF THE PREFERRED EMBODIMENTS

Figure 1:
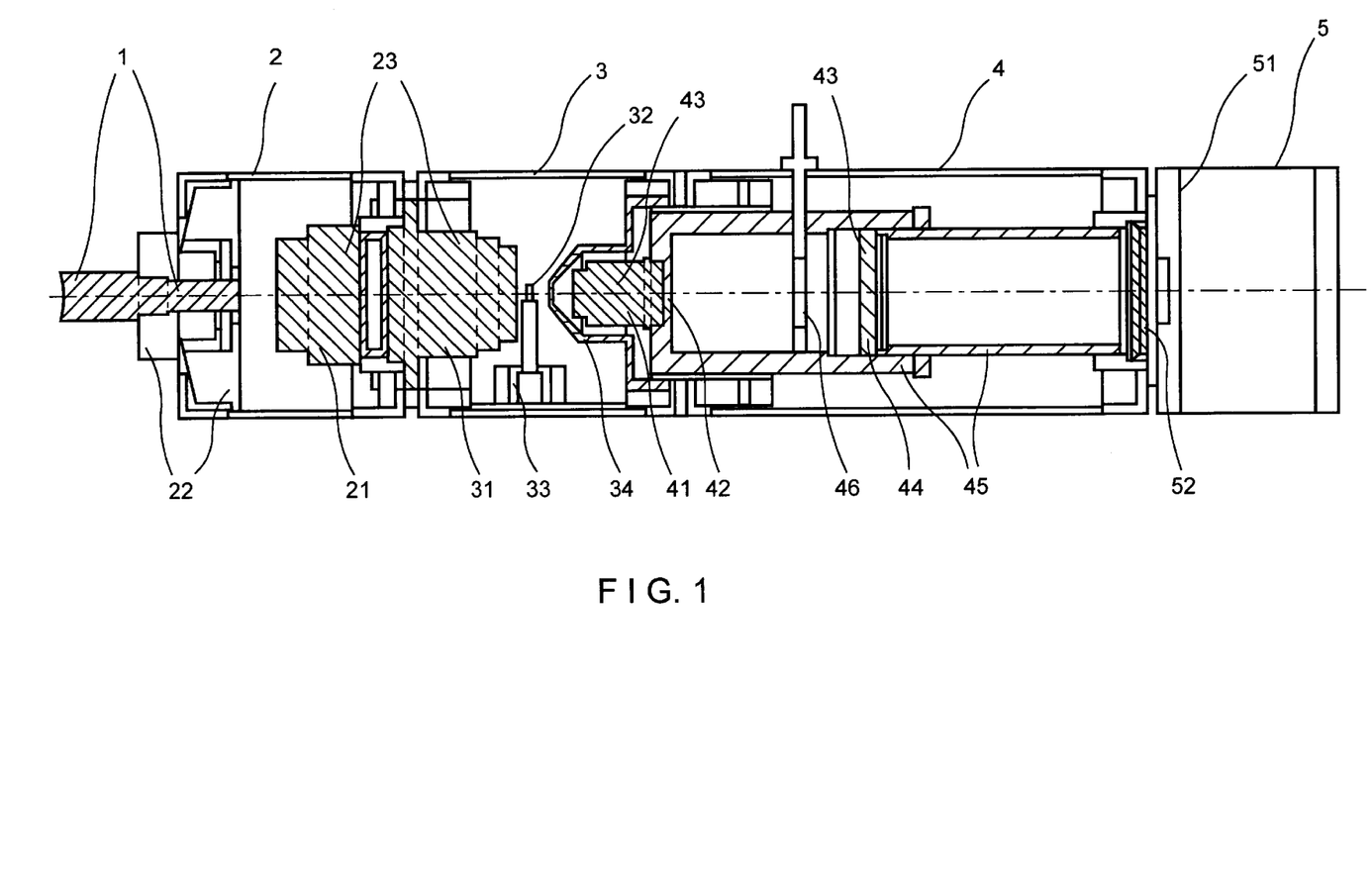
FIG. 1 shows an embodiment of the arrangement according to the invention in modular construction.
Figure 5:
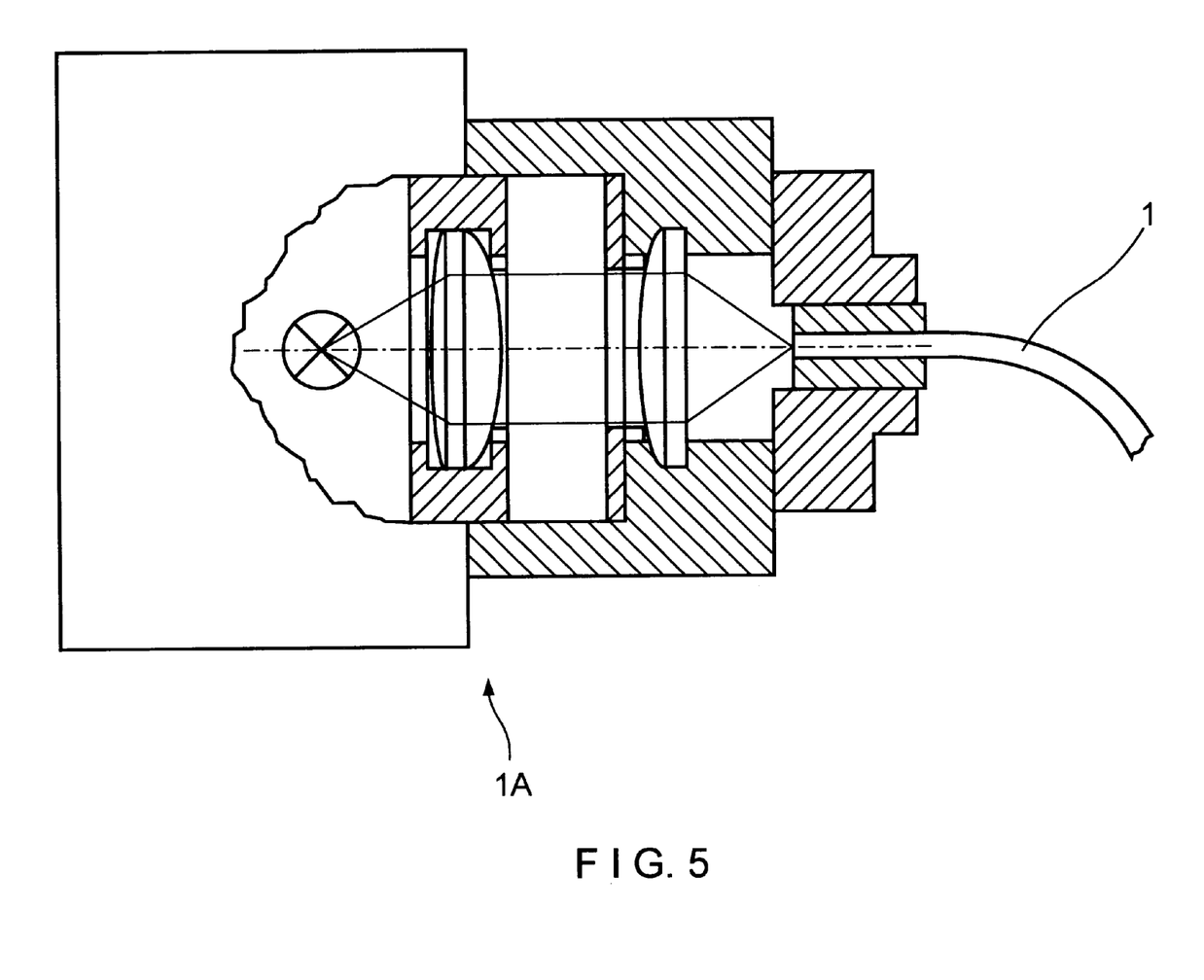
FIG. 5 depicts a typical light source.

As can be seen from FIG. 1, the arrangement according to the invention, in its basic construction, comprises a light source unit 1A (See FIG. 5) which provides, via a coupled light guide 1, excitation light that is adapted spectrally to the utilized fluorescing substance, as well as illumination optics 23, a substrate 32, transmitting optics 43 with a limiting aperture stop 42, and a receiver in the form of a CCD camera 51. All optical components are constructed in modules; a light source module with connected light guide 1 for providing the excitation light, an illumination module 2 for coupling in light and for beam expansion, a substrate carrier module 3 and an imaging module 4 for imaging the fluorescence radiation generated by the substrate 32 on the CCD camera 51 contained in a camera module 5. The modular construction enables a simple adaptation of the arrangement according to the invention to specific requirements for analyzing a wide variety of substrates 32 which can range from nanotiter plates and spotted glass slides to biochips with several tens of thousands of spots. The construction depicted in FIG. 1 assumes—without limiting its generality—a substrate 32 in the form of a biochip with 20,000 in which a biochip 32 can be read out as whole and substrate movement by means of a substrate displacement unit 33 is necessary only to feed the next biochip 32.

The illumination light exiting from the light guide 1 is received by the illumination optics 23 and transmitted for illuminating the biochip 32. For this purpose, a suitable light guide holder 22 at the input of the illumination module 2 following the light source module provides for coupling in light and for beam shaping for proper locking and alignment of the light guide 1 relative to the illumination optics 23. The illumination optics 23 realize a transmitted-light darkfield process with respect to the biochip 32 and comprise a collector 21 and a dry darkfield condenser 31. The collector 21 first collects the light source radiation exiting in a divergent manner from the light guide 1 before the darkfield condenser 31 realizes a ring-shaped illumination in such a way that the limiting or inner aperture angle of the illumination is appreciably greater than the given aperture angle of the objective 41 of the transmitting optics 43. The increased aperture angle of the darkfield condenser 31 serves to cut out diffracted excitation radiation passing through the biochip 32 so that it cannot enter the aperture of the objective 41. Further, a suitably shaped stray light baffle 34 is arranged in front of the objective 41 for shielding from unwanted scatter light.

As a result of the excitation radiation which impinges indirectly via the darkfield condenser 31, the fluorescing substances contained in the biochip 32 emit fluorescence radiation which is to be determined quantitatively for each individual substrate pixel of the biochip 32. An exact correlation of the imaging of the fluorescence radiation of each individual substrate pixel to a determined group of receiver elements of the CCD camera 51 is realized for this purpose, wherein crosstalk of the fluorescence radiation originating from a determined substrate pixel of the biochip 32 to receiver pixels of the CCD camera 51 that are not correlated to it must be extensively eliminated due to the falsification of measured values.

For simultaneous detection of the greatest possible number of substrate pixels of the biochip 32 to be read out (in this case, even all of these substrate pixels), optical imaging is realized with a high-aperture micro-objective 41 (e.g., EPI-PLAN® 10×0.2 micro-objective) in conformity to the general teaching of fluorescence analysis. In order to suppress the above-mentioned crosstalk of the fluorescence radiation, an additional aperture stop 2 is arranged in the aperture stop plane (possibly also in a conjugated plane) located outside of the objective 41, which reduces the indicated aperture of the micro-objective 41 (by about 25%) to 0.16 to 0.15. As is shown in FIG. 1 using the example of a micro-objective 41 with external aperture stop plane, the additional aperture stop 42 is, most simply, integrated in the screw mount of the objective 41 and can therefore be accounted for during the manufacture of the fixed part of the tube 45.

Figure 2:
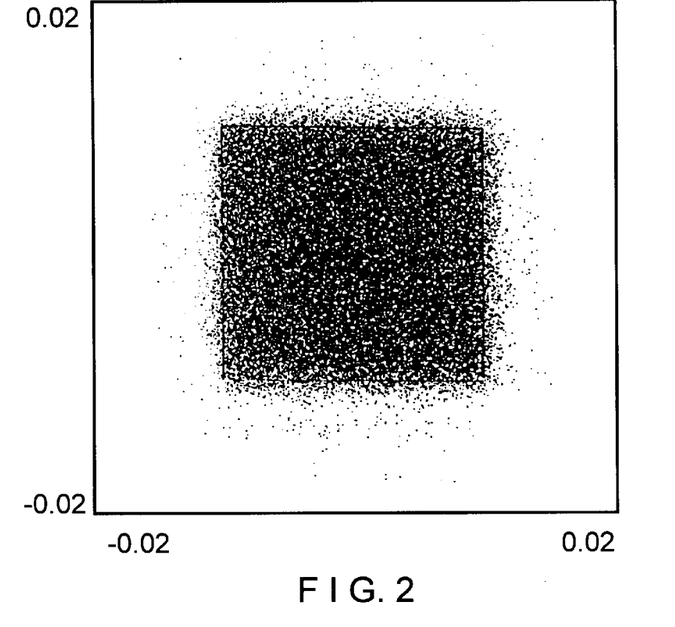
FIG. 2 shows an intensity distribution of the fluorescence radiation of a substrate pixel with imaging on the receiver without a reduction of the aperture of the objective.
Figure 3:
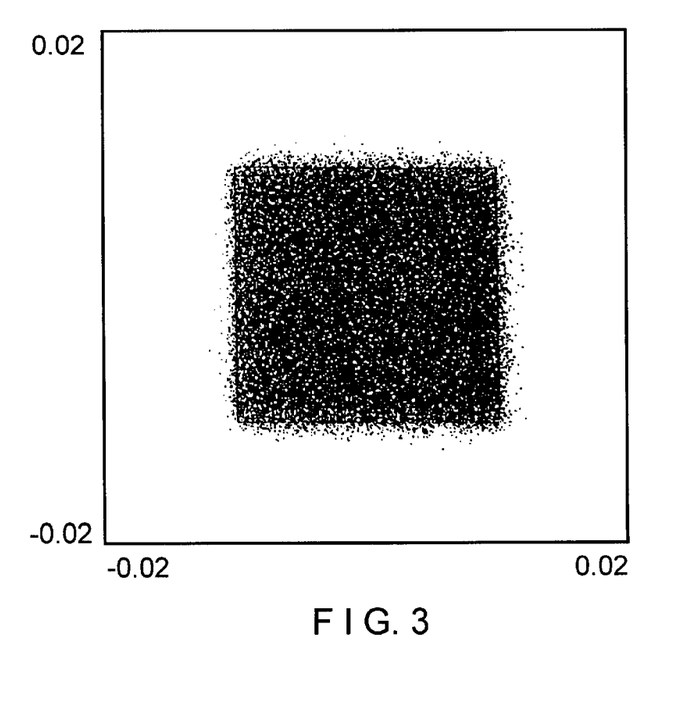
FIG. 3 shows an intensity distribution of the fluorescence radiation of a substrate pixel with imaging on the receiver with a reduced aperture of the objective.

The effect of the additional aperture stop 42 can be clearly seen from a comparison of FIGS. 2 and 3. FIGS. 2 and 3 show the effect whereby the fluorescence energy can be better concentrated on the receiver element and its immediate surroundings with a smaller aperture. This means that a substantial portion of the fluorescence energy obtained with a large numerical aperture of the objective 41 (according to FIG. 2) not only cannot be utilized by the associated receiver element, but can even lead to a falsification of the measured values of the neighboring receiver elements. Consequently, when reading out (according to the camera principle, as it is called) small and closely adjacent fluorescing elements of a biochip 32, the requirement for the largest possible imaging aperture for quantitative fluorescence analysis is not always meaningful. This can be attributed essentially to the fact that with real optically imaging elements imaging errors (aberrations) which cannot be corrected or which cannot be adequately corrected are always present, so that the fluorescence light of the individual substrate pixels is mixed together (superimposed). According to FIG. 3, on the other hand, because of the reduction of the aperture of the utilized micro-objective 41 by means of the additional aperture stop 41, the fluorescence light scattering is clearly reduced in relation to the intensity distribution with a normal (full) aperture of the same objective 41 as that used for the recording in FIG. 2.

In general, the amount by which the numerical aperture of the utilized objective is reduced depends, on the one hand, on the numerical aperture itself and, on the other hand—to a considerably greater extent—on the correction factor of the aberration of the objective. In currently available micro-objectives with a numerical aperture between 0.2 and 0.25, a reduction of the numerical aperture of 15 to 30% is generally sufficient for suppressing crosstalk of fluorescence light on neighboring pixels. It is noted for the sake of comparison that a reduction by up to 50%, sometimes even up to 65%, is required when using good photographic objectives with similar aperture values for sufficient suppression of crosstalk as is shown in FIG. 3.

The fluorescence light excited in the substrate pixels of the biochip 32 is detected in part by the micro-objective 41, limited by the additional aperture stop 42 and imaged on the CCD camera 51 via subsequent optical elements. Since the utilized micro-objective 41 images the biochip 32 to infinity, the transmitting optics 43 are supplemented by a tube lens 44 which provides for a sharp imaging of the substrate pixels of the biochip 32 in the plane of the receiver elements of the CCD camera 51 by means of an adjustable tube 45 and camera adapter optics 52. By means of the tube 45 and the tube lens 43 located therein, imaging is realized in such a way that a group of receiver elements (e.g., 4, 9, 16 or 25) of the CCD camera 51 is uniquely assigned to each substrate pixel. The optical distances between the above-mentioned elements—the micro-objective 41, tube lens 44 and camera adapter optics 52—are freely selectable within certain limits in the tube 45 since, in contrast to a conventional microscope beam path in which chromatic aberrations are generally corrected only in cooperation with the imaging optics in their entirety, the imaging need only be realized for a narrow chromatic range of fluorescence radiation.

Further, a filter 46 (arranged directly in front of the receiver as far as possible) for passing the fluorescence radiation and blocking the excitation radiation is arranged inside the tube 45 in front of the tube lens 44 and can be exchanged depending on the fluorescent dye in the biochip 32 corresponding to the fluorescence wavelength to be detected.

The camera module 5 contains a cooled (e.g., by a Peltier element) CCD camera 51 in order to achieve a high signal-to-noise ratio by suppression of thermal noise even over long integration times of the CCD (from several seconds to several minutes). Accordingly, the loss of fluorescence energy resulting from the reduced objective aperture can also be at least partially compensated in this way by lengthening the integration time of the CCD camera 51.

However, in view of the desired large specimen throughput in fluorescence analysis of biochips, long integration times are only tenable under certain conditions, so that the weakening of the fluorescence radiation incident on the CCD camera 51, which occurs as a result of the aperture of the objective 41 reduced by means of the additional aperture stop 42, must be compensated by additional suitable steps.

In this connection, the first effective step is a better adaptation of the excitation radiation to the excitation wavelength of the fluorescing substances. However, the difficulty in this regard consists in exciting at the same intensity all fluorescent dyes which are commonly used in biochip analysis for detecting determined contents (e.g., DNA sequences) and which have different excitation wavelengths and, accordingly, making the fluorescence measurements of different substrates comparable also when different fluorescing substances are used. For this reason, an intensive light source with a continuous spectrum, e.g., a halogen lamp, is used. The emitted radiation of the halogen lamp can then be freely selected with a virtually uniform intensity for any fluorescing substances in a manner known per se by means of an excitation filter which passes in a narrow band the optimum excitation wavelength of the fluorescent dye used in the biochip 32.

Figure 4:
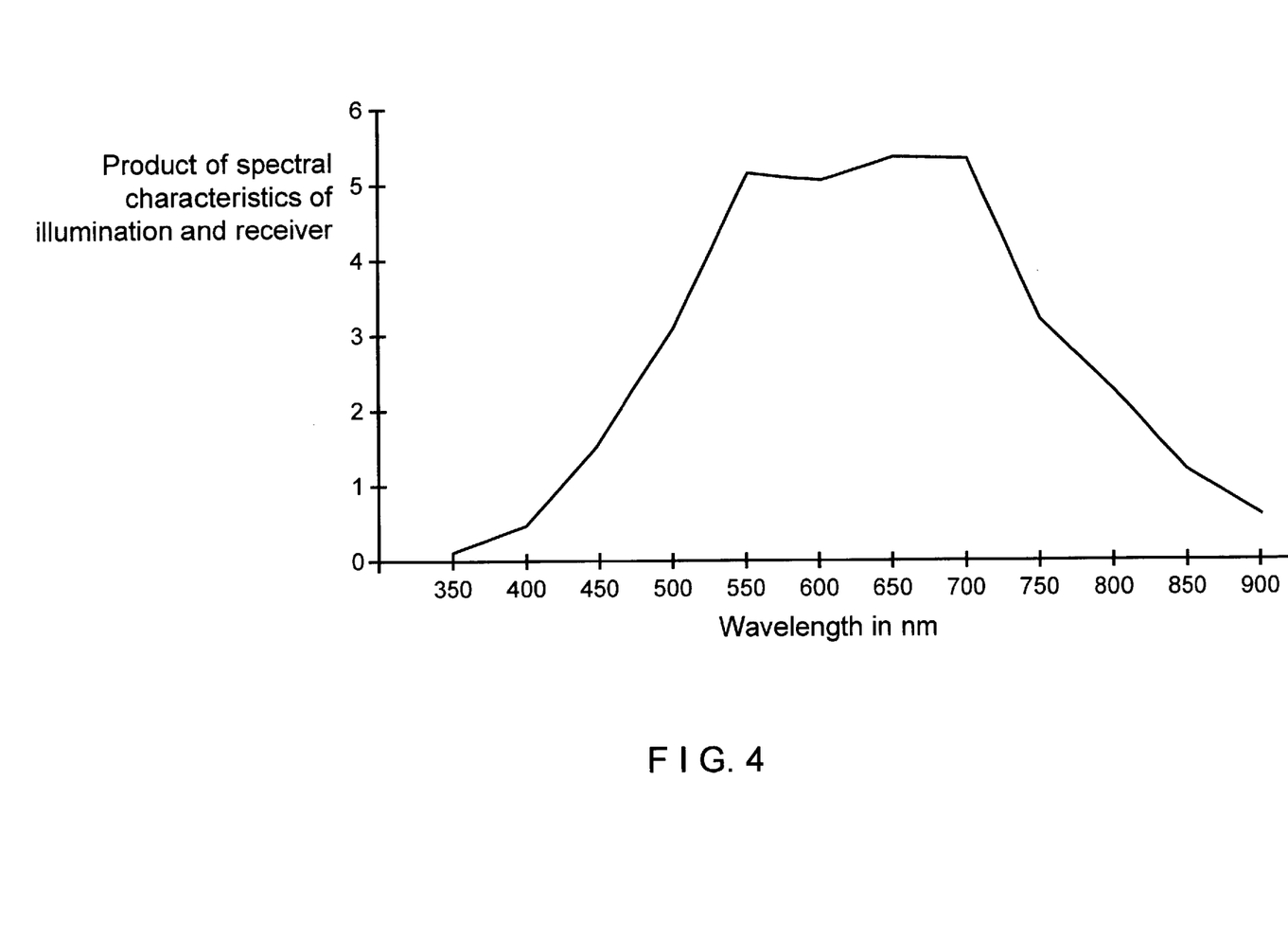
FIG. 4 depicts the spectral characteristics of the light source, liquid light guides and receiver.

A second step promoting measurable fluorescence intensity of the substrate pixels of the biochip 32 consists in adapting the spectral characteristics of the illumination and receiver. For this purpose—taking as a basis the specific construction of the invention according to FIG. 1—on the illumination side, the spectral emission of the light source and the spectral transmission of the light guide 1 and, on the reception side, the spectral sensitivity of the CCD camera 51 are so configured that the product of these quantities virtually results in a constant over the range of required excitation wavelengths and fluorescence wavelengths. FIG. 4 shows the results that were achieved for the halogen lamp used in the example, with the light guide 1 in the form of a LUMATEC Ser. 380 liquid light guide and the CCD camera 51 with a FT 1010 CCD chip.

Strictly speaking, the product of the spectral emission of the light source and the spectral transmission of the light guide 1 on the excitation wavelength and the spectral sensitivity of the receiver on the emission wavelength of the fluorescence radiation would actually have to be a constant. However, since the excitation wavelengths and the associated fluorescence wavelengths of the commonly used fluorescent dyes are only separated by several tens of nm, this slight imprecision can be disregarded when the product of the spectral characteristics is sufficiently constant over the entire necessary wavelength range.

The above-mentioned steps for improving the yield of fluorescence light when the effective aperture of the objective 41 is reduced according to the invention make it possible to achieve the quantity of fluorescence light on the receiver elements of the CCD camera 51 that is necessary for a quantitative evaluation of every substrate pixel without having to tolerate a reduction in chip throughput during fluorescence readout because of considerably increased CCD integration times.

While the foregoing description and drawings represent the preferred embodiments of the present invention, it will be obvious to those skilled in the art that various changes and modifications may be made therein without departing from the true spirit and scope of the present invention.

LIST OF REFERENCE NUMBERS

1 light guide
2 illumination module
21 collector
22 light guide holder
23 illumination optics
3 substrate carrier module
31 darkfield condenser
32 biochip (substrate)
33 substrate displacement unit
34 scatter light baffle
4 imaging module
41 (micro-)objective
42 additional aperture stop
43 transmitting optics
44 tube lens
45 tube
46 filter
5 camera module
51 CCD camera
52 camera adapter optics

What is claimed is:

1. An arrangement for the detection of the fluorescence radiation of matrix-shaped specimen carriers, said arrangement comprising:
    a large number of individual specimens presenting metrically ordered pixels on a substance and emitting a fluorescence radiation that is characteristically influenced by the respective specimen substance;
    an illumination device for simultaneous excitation of the fluorescence radiation of a large number of substrate pixels, containing a light source and a spectrally narrow-band excitation filter which can be exchanged depending on the fluorescing substance;
    transmitting optics for transmitting the fluorescence radiation emitted by individual substrate pixels to a receiver with a large number of receiver elements;
    an exchangeable filter disposed in front of the receiver for passing the fluorescence wavelength and blocking excitation wavelengths;
    the transmitting optics containing an imaging objective by which every substrate pixel is correlated with a determined group of receiver elements of the receiver and which is outfitted with an additional aperture stop for limiting the angular area of the fluorescence radiation detected by the objective, so that the receiver elements which are correlated respectively with a determined substrate pixel receive substantially no fluorescent light of neighboring substrate pixels;
    said illumination device having a darkfield illumination unit for large-area illumination of a large number of substrate pixels by formation of an excitation beam bundle which is symmetric with respect to the axis of the objective and which cuts out the aperture of the objective as well as a substantial angular area surrounding the objective aperture.

2. The arrangement according to claim 1, wherein the objective is a micro-objective.

3. The arrangement according to claim 2, wherein the aperture of the micro-objective is reduced by 10 to 30% by the additional aperture stop.

4. The arrangement according to claim 2, wherein the objective is a micro-objective with an aperture stop plane which is located outside of the objective, wherein the additional aperture stop is arranged in this aperture stop plane.

5. The arrangement according to claim 4, wherein the objective is a micro-objective with ten-times magnification and an aperture of 0.2 to 0.25, wherein the effective aperture of the micro-objective is reduced by 15 to 30% by the additional aperture stop.

6. The arrangement according to claim 1, wherein a configuration of light guides which is arranged symmetrically about the axis of the objective is provided as darkfield illumination unit for illuminating the substrate, the outlet light of the light guides being directed so as to be focused on a spot of the substrate.

7. The arrangement according to claim 1, wherein a darkfield illumination unit is provided for transmitted light illumination for illumination of the substrate.

8. The arrangement according to claim 7, wherein the darkfield illumination unit for illumination of the substrate is a darkfield condenser.

9. The arrangement according to claim 8, wherein the darkfield illumination unit for illumination of the substrate is a dry darkfield condenser.

10. The arrangement according to claim 8, wherein a collector is arranged in front of the darkfield condenser.

11. The arrangement according to claim 1, wherein, in order to make fluorescence radiation measurements comparable when exciting with different excitation wavelengths, the spectral emission of the illumination device and the spectral sensitivity of the receiver are adapted to one another in such a way that their product gives approximately a constant over a wavelength range required for the fluorescence substances to be detected.

12. The arrangement according to claim 11, wherein for the purpose optimum excitation of fluorescence radiation of different fluorescing substances, an intensive continuous light source with an exchangeable bandpass filter adapted to the excitation wavelength of the fluorescing substance is provided.

13. The arrangement according to claim 11, wherein the light source is a halogen lamp.

14. The arrangement according to claim 11, wherein the light source is a xenon lamp.

15. The arrangement according to claim 11, wherein the light source is coupled with the darkfield illumination unit via a light guide.

16. The arrangement according to claim 15, wherein the light guide is a liquid light guide.

17. The arrangement of claim 1, wherein
    the illumination device consists of the light source and the darkfield illumination unit, which are separate light source and illumination modules, the illumination module being provided for coupling in the incoming light of the light source module and beam shaping;
    the substrate with the large number of metrically ordered individual specimens is held in a substrate displace ment unit within a substrate carrier module being able to take hold of said illumination module;

the transmitting optics for transmission of fluorescence radiation of the substrate to the receiver are arranged in an imaging module including the imaging objective with the additional aperture stop;

the receiver is formed as a camera module being connected downstream the imaging module;

said light source, illumination, substrate carrier, imaging, and camera modules are assembled in exchangeable modules for adapting to specific cases of application.

18. The arrangement of claim 17, wherein said light source module is connected to the illumination module by a light guide, the illumination module is fitted to the substrate carrier module, the objective of the imaging module is inserted into said substrate carrier module opposite to the input of the illumination module, and the camera module is arranged downstream the imaging module, wherein the substrate carrier module in particular contains a displacement unit for recording large-area substrates and for successive processing of large substrates or substrate arrays.

* * * * *